United States Patent
Crisp

(10) Patent No.: US 7,495,146 B2
(45) Date of Patent: Feb. 24, 2009

(54) WOUND DRESSING

(75) Inventor: William E. Crisp, Paradise Valley, AZ (US)

(73) Assignee: Vivo Ltd. Partnership, Paradise Valley, AZ (US)

( * ) Notice: Subject to any disclaimer, the term of this patent is extended or adjusted under 35 U.S.C. 154(b) by 0 days.

(21) Appl. No.: 11/130,800

(22) Filed: May 17, 2005

(65) Prior Publication Data

US 2006/0015053 A1    Jan. 19, 2006

Related U.S. Application Data

(63) Continuation-in-part of application No. 10/891,566, filed on Jul. 15, 2004, now abandoned.

(51) Int. Cl.
*A61F 13/00* (2006.01)
*A61N 1/30* (2006.01)

(52) U.S. Cl. .............................. 602/48; 604/20; 604/46; 602/2

(58) Field of Classification Search ............. 602/41–43, 602/48, 2; 604/19, 46, 174, 289–291
See application file for complete search history.

(56) References Cited

U.S. PATENT DOCUMENTS

| 222,276 | A | * | 12/1879 | Hunter ........................ 604/20 |
| 4,265,233 | A | * | 5/1981 | Sugitachi et al. ............. 604/304 |
| 4,767,401 | A | | 8/1988 | Seiderman |
| 5,288,289 | A | * | 2/1994 | Haak et al. .................... 604/20 |
| 5,298,017 | A | * | 3/1994 | Theeuwes et al. ............. 604/20 |
| 5,685,837 | A | | 11/1997 | Horstmann |
| 5,759,570 | A | * | 6/1998 | Arnold ........................ 424/443 |
| 5,814,094 | A | * | 9/1998 | Becker et al. ................. 607/50 |
| 6,181,963 | B1 | * | 1/2001 | Chin et al. .................... 604/20 |
| 6,306,419 | B1 | | 10/2001 | Vachon et al. |
| 6,365,220 | B1 | | 4/2002 | Burrell et al. |
| 6,522,918 | B1 | * | 2/2003 | Crisp et al. ................... 604/20 |
| 6,861,570 | B1 | | 3/2005 | Flick |
| 2004/0049145 | A1 | * | 3/2004 | Flick ............................ 602/41 |
| 2005/0085751 | A1 | * | 4/2005 | Daskal et al. ................. 602/2 |
| 2006/0035975 | A1 | * | 2/2006 | Keith et al. .................. 514/566 |

\* cited by examiner

*Primary Examiner*—Kim M Lewis
(74) *Attorney, Agent, or Firm*—Barbara E. Johnson, Esq.

(57) ABSTRACT

A wound dressing or bandage that provides a galvanic current for extended periods of time before having to change the dressing or bandage is addressed in the present invention. The present invention is directed to a galvanic current wound dressing having antimicrobial properties and to a method for treating a patient with the wound dressing.

13 Claims, 9 Drawing Sheets

WOUND DRESSING

CROSS REFERENCE TO RELATED APPLICATIONS

This application is a Continuation-In-Part of U.S. patent application Ser. No. 10/891,566, filed Jul. 15, 2004, which is herein incorporated by reference in its entirety.

BACKGROUND OF THE INVENTION

1. Field of the Invention

The present invention relates to an apparatus for attacking microbes, namely, bacteria, viruses, and fungi. More particularly, the present invention is a sustained release galvanic current bandage or gauze for use as a wound dressing.

2. Description of Related Art

The art of applying a low voltage electric current to control microbes and promote healing action for medical and hygienic purposes has been developing for many years. In particular, it is known that the use of a low voltage electric field applied through a reservoir can be used to deliver drugs or agents in the reservoir systematically or to produce a localized therapeutic effect. Moreover, the application of electricity to the body, with or without drugs or agents, can be used therapeutically. Direct current fields can exert a microbicidal effect, and electric voltage can also, via electrophoresis, induce agents or medications to penetrate tissue more deeply, and can induce the agents to penetrate structures or implants such as biofilms. Further therapeutic effects of electricity include control of pain, edema and acceleration of wound healing. Moreover, the localized effect of drugs and agents can be greater at the delivery site than the effect that is seen with topically or systemically delivered agents alone, due to higher available concentrations at the site, over time.

Silver has been used as a disinfectant for centuries. The use of medicinal silver was diminished by the advent of more versatile and effective antibiotics. The misuse of antibiotics coupled with bacteria's ability to mutate have resulted in resistant organisms and reawakened interest in silver's effective antimicrobial properties. Elemental silver is an effective microbicide in solutions as dilute as one part per 100 million. Silver ions kill micro-organisms by blocking the respiratory system, which is the process of harvesting energy by transferring electrons from an electron donor to an electron receptor.

Although salts of silver will immediately supply the bactericidal qualities of silver to a wound, they also impair wound healing. Ionic silver decreases the inflammatory process in a wound, decreases edema, and increases blood supply to the wound. Silver alone decreases wound surface zinc, which is required for metalloproteinase (MMP) activity modulation. Silver and zinc together also increase wound calcium which increases the wound re-epithelization rate. Matrix MMPs are a group of proteolytic enzymes that are vital in various modeling repairs and the inflammatory processes of wound healing. There are now 20 MMPs identified. MMPs are dependent on intrinsic zinc ions and extrinsic calcium for full activity in modifying the inflammatory response by binding histidine. MMPs are produced by a number of important cells vital to wound repair. For example, neutrophils, macrophages, keratinocytes, and fibroblasts are expressed in physiologic repair, remodeling and epithelial proliferation in wounds.

Low voltage antibacterial devices are able to infuse charged molecules, i.e., iontophoresis, as well as uncharged molecules into the body, i.e., electro-osmosis. For example, U.S. Pat. No. 5,298,017 to Theeuwes et al. (the '017 patent), which is incorporated herein by reference, describes an iontophoretic process by which drugs are delivered transdermally or transmucosally under the influence of an electrical potential. Iontophoretic devices use two distinct electrodes, with at least one of the electrodes being applied to the body. These devices typically utilize a conventional electric power source, such as a battery, to develop the electric current. In some cases, the power source is located separately from the device and in some cases the power source is integrated into the device. These devices also rely solely on the creation of a discrete ion pathway incorporating the body or tissue to effect an electromotive force via forms defined by the sequence of a first electrode, tissue and a second electrode.

There are devices described in the prior art that rely on the electric field generated by the device itself. The power source generally provides no therapeutic value itself other than to provide the electric current necessary to drive the iontophoretic or electro-osmotic device to deliver an agent that is different from the electrode metals. Further, if the power supply should fail for any reason, the device is typically rendered useless. Also, where the power source is located away from the device, limitations are imposed on patient mobility. Still further, even when the prior art integrates the conventional power source into the device, there are limitations. In particular, the prior art makes it clear that the conventional power source must be protected from short circuiting itself. Consequently, great lengths have been taken to insure that the two electrodes are insulated in order to limit the possibility of a short circuit. Further limitations of these devices include high cost due to wires, electrical insulation, battery failure, problems with user compliance, maintenance, and damage.

In spite of the fact that the use of external power sources is prevalent in the art of iontophoresis and electro-osmosis, it is known to rely exclusively on the electric potential generated by the galvanic couple between dissimilar materials, e.g., a zinc electrode and a silver/silver chloride counter electrode, to deliver a drug. For example, the embodiment of the device illustrated in FIG. 2 of the '017 patent does not use an external power source. While the primary purpose of such devices is to deliver a drug present in a drug reservoir, as a consequence of the galvanic couple, ions of the materials used for the anode and/or cathode are delivered into the body. Unfortunately, because the anode and cathodes of such prior art devices are typically made from materials having a relatively low total surface area, the rate of metallic ion transfer from the metallic electrodes is typically lower than desired for satisfactory therapeutic effects.

As described in U.S. Pat. No. 5,814,094 to Becker et al. (the '094 patent), iontophoretic devices that provide silver ions for wound healing are known. Use of silver-coated nylon as the anode for the iontophoretic device of the device of the '094 patent provides a relatively high total surface area material as the source of silver ions. However, the device of the '094 patent features the use of an external power source connected to the silver-coated nylon anode to generate the electrical potential that drives the silver ions into the body, and so suffers from the limitations of other iontophoretic devices described above.

U.S. Pat. No. 6,522,918 to Crisp et al. (the '918 patent), which is incorporated herein by reference, describes electrolytic devices for use in treating tissue through the use of a silver-bearing material and a metal other than silver with no external voltage source necessary. However, one of the disadvantages of the devices of the '918 patent is that the devices are limited in usefulness due to their inherent short-lived duration of action.

Therefore, a need exists for a wound dressing bandage or gauze that provides a galvanic current for extended periods of time before having to change the bandage or gauze.

SUMMARY OF THE INVENTION

The foregoing need for a wound dressing or bandage that provides a galvanic current for extended periods of time before having to change the dressing or bandage is addressed in the present invention. The present invention is directed to a galvanic current wound dressing having antimicrobial properties and to a method for treating a patient with the wound dressing.

The wound dressing bandage or gauze comprises an outer layer composed of polypropylene, polyethylene, polyethylene terephthalate, rubbers, copolymers or silicones and a carrier layer composed of fluid soluble material, such as pre-cured polypropylene or pre-cured polyethylene. The carrier layer is attached to the outer layer. It is important to note that the outer layer is not essential to the invention. The carrier layer includes a plurality of first metal particles having an electrochemical potential and a plurality of second metal particles having a different electrochemical potential from the plurality of first metal particles. The first particles consist of pure or nearly pure silver, and/or suitable salts and oxides thereof. The second particles consist of pure or nearly pure aluminum, cobalt, copper, gold, iron, magnesium, platinum, titanium or zinc, and/or suitable salts and oxides thereof. The first metal particles and second metal particles are suspended alternatively within the fluid soluble carrier layer, whereby a sustained-release galvanic current is produced between the first metal particles and the second metal particles when the carrier layer is subjected to fluids, which function as an electrolyte, causing erosion of the carrier layer. The first and second metal particles are spaced between 0.1 mm to 7.0 mm apart, but preferably spaced less than 2.0 mm apart. The sustained galvanic current produced by the wound dressing is between 0.1 to 1.0 millivolts, but preferably about 0.2 millivolts. The wound dressing may be a bandage having an adhesive portion. The wound dressing may also be a wound dressing gauze.

The present invention is also directed toward a method of treating a patient with a wound dressing, comprising the steps of:

(i) providing to a patient a wound dressing comprising:

a carrier layer, said fluid soluble carrier layer includes a plurality of first metal particles having an electrochemical potential, a fluid soluble material, and a plurality of second metal particles having a different electrochemical potential from said plurality of first metal particles, wherein said first metal particles and said second metal particles are suspended alternatively within said fluid soluble material, whereby a sustained-release galvanic current is produced between said first metal particles and said second metal particles when said carrier layer is subjected to electrolyte-containing fluids causing erosion of said carrier layer;

(ii) applying to said patient said wound dressing; and (iii) removing said wound dressing from said patient at seven to ten days after step (ii).

DETAILED DESCRIPTION OF THE INVENTION

Figure 1:
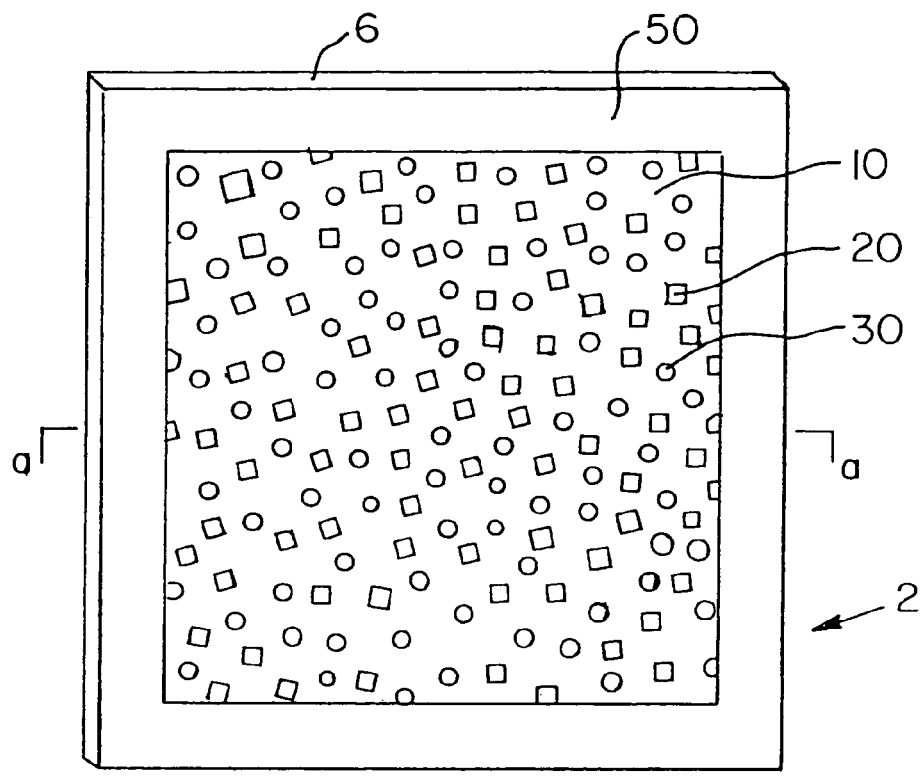
FIG. 1 is a perspective view of the dermal side of one embodiment of the present invention.

Referring to the drawings in which like reference characters refer to like parts throughout the several views thereof, FIGS. 1-5 illustrate a wound dressing in accordance with the present invention and the related features. The absence of shading in the Figures in no way reflects the presence or absence of a particular characteristic of the wound dressing.

Figure 2:
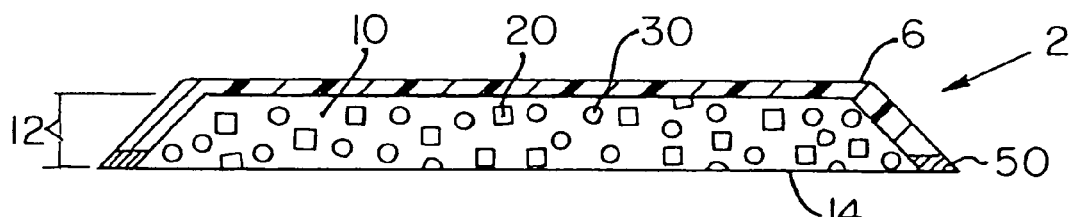
FIG. 2 is a sectional view of the present invention taken on line a-a of FIG. 1.
Figure 3:
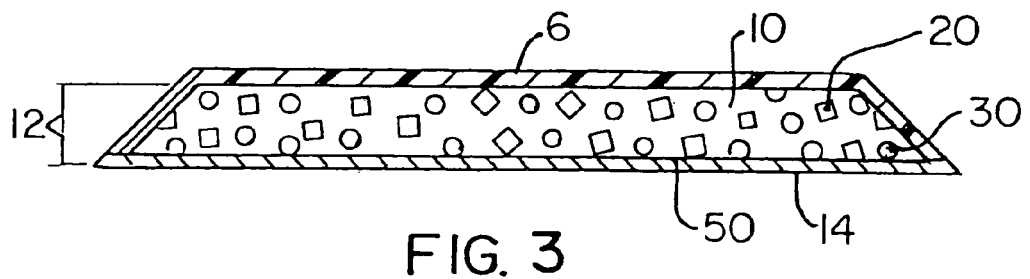
FIG. 3 is a sectional view of the present invention showing a modification of the embodiment of the invention of FIG. 1.
Figure 4:
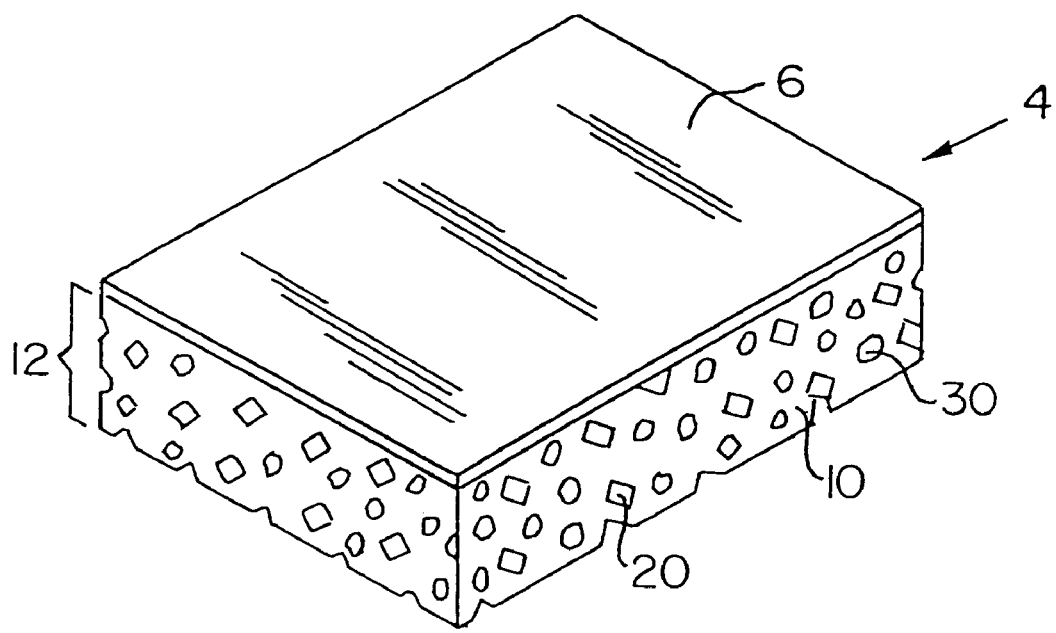
FIG. 4 is a perspective view of a second embodiment of the present invention.
Figure 5:
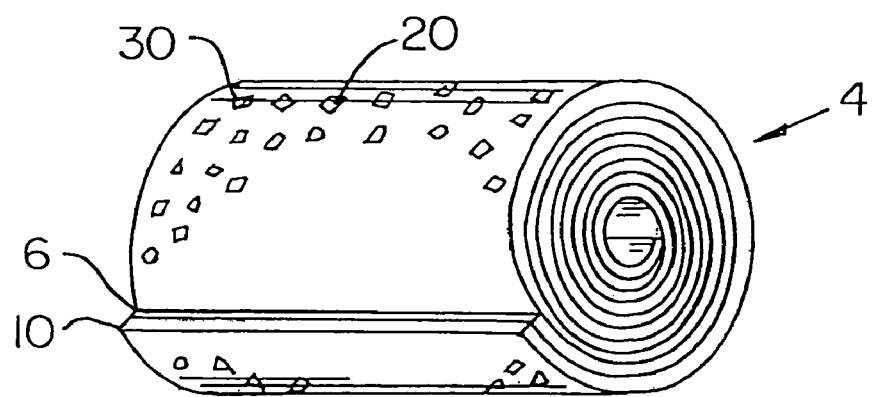
FIG. 5 is a perspective view of the second embodiment of the present invention shown in FIG. 4 rolled about its central axis so as to form a cylinder.

As shown in FIGS. 1-3, a first embodiment of the present invention, a wound dressing bandage 2, includes an outer layer 6, a carrier layer 10, silver particles 20, other metal particles 30, and an adhesive portion 50. As shown in FIGS. 4-5, a second embodiment of the present invention, a wound dressing gauze 4, includes an outer layer 6, a carrier layer 10, silver particles 20, and other metal particles 30.

More particularly, the outer layer 6 of the present invention is made of polypropylene, polyethylene, polyethylene terephthalate, rubbers, copolymers, silicones, other polyalkylenes, or other suitable materials now known or heretofore developed in the art. Further, the outer layer 6 may be composed of any bioabsorbable or biocompatible material. Additionally, the outer layer 6 may be made of a polyester material of sufficient mechanical strength in order to resist exposure to water and minimal physical touching, such as the brushing of a hand or clothing against the surface of the outer layer. The outer layer 6 may be translucent or opaque.

The carrier layer 10 of the present invention is composed of a fluid-soluble material, preferably a pre-cured polypropylene or a pre-cured polyethylene. However, other polyalkylene materials may be used for the carrier layer 10. As depicted in FIGS. 2-4, the carrier layer 10 has a thickness 12 which enables the suspended silver particles 20 and other metal particles 30 to be suspended in multiple horizontal zones throughout the carrier layer 10. Individual spots or aliquots of the silver particles 20 and other metal particles 30 should be spaced in patterns by which the metal types alternate and the spots or aliquots range in spacing from almost touching (such as 0.1 mm) up to approximately 7.0 mm apart, preferably less than 2.0 mm apart. The deposition of the silver and other metal particles, 20 and 30 is preferably conducted by dispersing the particles separately in the pre-cured polyalkylene material and depositing grids of the metals on the outer layer 10. The spots or aliquots may by laid down by silk screening, or presumably can be arrayed by any other means now known or heretofore developed in the art, including ink jet printing and thin film applications. Generally, one metal particle type is applied to the carrier layer 10 at a time and allowed to dry before a second metal particle type is applied. This allows for consistent delivery of the silver particles 20 and other metal particles 30 to the wound surface as the metal deposits slowly degrade.

The silver particles 20 of the present invention are preferably silver that is at least 99.99% to 99.9999% pure. However, less pure silver, and suitable salts and oxides thereof may be used. Examples of other silver particles 20 that may be used include: silver fluorides, silver chlorides, silver bromides, silver iodides, silver oxides, silver sulfides, silver selenides, and silver tellurides. Preferably, the diameter of the silver particles 20 is between 0.1 to 1.0 microns, however, the diameter may vary.

The other metal particles 30 of the present invention are preferably zinc, however other metal particles that will create a galvanic charge when adjacent to silver may be used. Examples of other metal particles 30 that may be used according to the present invention include aluminum, cobalt, copper, gold, iron, magnesium, platinum, titanium and zinc, and salts and oxides thereof. The other metal particles 30 are desirably pure or nearly pure zinc, but aluminum, cobalt, copper, gold, iron, magnesium, platinum and titanium may also be used. In addition, the other metal particles 30 may comprise compounds providing free dissolution of metal ions, such as zinc gluconate, zinc acetate, zinc chloride, zinc citrate, zinc propionate, zinc sulphate heptahydrate, zinc butyrate, zinc formate, zinc glycolate, zinc glycerate, zinc lactate, zinc sulfate, ferrous oxide, ferrous sulphate, and titanium oxide. Other zinc salts which are soluble in water and have low pK values, which indicate a high rate of zinc ion release, may also be used. Other suitable metal salts and compounds that release metal ions upon exposure to an aqueous medium may also be used. Preferably, the diameter of the other metal particles 30 is between 0.1 to 1.0 microns, however, the diameter may vary.

The adhesive portion 50 of the first embodiment of the present invention is made of conventional adhesives now known or heretofore developed in the art. The adhesive portion 50 is used to adhere the bandage 2 to a patient's skin surface. The adhesive should provide a strong fixation of the bandage 2 on the skin, but should also be able to allow removal of the patch by the patient. In other words, the bandage is not meant to be permanently affixed to a patient's body. As shown in FIGS. 1 and 2, the adhesive portion 50 may be present along the periphery of the skin surface side of the bandage 2. Alternatively, as shown in FIG. 3, the adhesive portion 50 may be flush all along the body surface side 14 of the carrier layer 10. When the bandage 2 is designed as shown in FIG. 3, it is important that the adhesive portion 50 be composed of a water-permeable adhesive. This ensures that physiological body fluids will be able to penetrate the adhesive portion 50 in order to immediately contact the silver and other metal particles, 20 and 30, or to begin to erode the carrier layer 10. The physiological body fluids function as the electrolyte through which the metal ions pass to create electricity. Additionally, a peelable liner (not shown) is employed when the first embodiment of the present invention is manufactured in order to prevent the adhesive portion 50 from prematurely sticking to a surface before the first embodiment of the present invention is used. The peelable liner of the present invention is constructed of a clear or opaque plastic material.

The first embodiment of the present invention, a wound dressing bandage 2, although illustrated in FIGS. 1-3 as square, or substantially square, may be made as any shape or size. For example, the wound dressing bandage 2 may be spherical, triangular, rectangular, etc. It may also be designed to fit a particular area of the body. For example, it can be larger in size to provide localized treatment to the back areas of a patient, or smaller in size to provide localized treatment to the fingers or toes of a patient.

The second embodiment of the present invention, a wound dressing gauze 4, although illustrated in FIGS. 4-5 as substantially square or rectangular, may also be made as any shape or size. For example, the wound dressing gauze 4, may be spherical, triangular, ovoid, etc. Preferably, the wound dressing gauze is of a rectangular shape in which rolls of the gauze may be manufactured, as shown in FIG. 5, allowing for desired lengths of the wound dressing gauze to be cut, depending on the surface that the wound dressing gauze 4 is to be applied. For instance, if the wound dressing gauze 4 is to be used to cover the circumference of a patient's arm, a long strip of the wound dressing gauze 4 may be cut and wrapped around the arm of the patient. Alternatively, if a smaller body surface is to be treated, such as the dorsal wrist surface of a patient, a small "patch" of the wound dressing gauze may be cut and applied to the wrist surface. The wound dressing gauze 4 may be fixably secured in place by tape, string, adhesive strips, or any other means now known or heretofore developed in the art. Additionally, it is to be appreciated that the wound dressing gauze 4 may also be inserted into body cavities or gaping flesh wounds for treatment. In this regard, the wound dressing gauze 4 is adapted for insertion in body cavities such as a nostril, the vagina, an ear, deep wound, fistula, or between body structures such as the gum and the inner wall of the cheek.

Discussing now the operation of the wound dressing bandage and gauze, 2 and 4, illustrated in FIGS. 1-5, the treatment of a large variety of pathologies may be encouraged through the use of the present invention, including without limitation, infections, cuts, incisions (including surgical incisions), abrasions, lacerations, fractures, contusions, burns, and amputations. During use, the bandage or gauze, 2 or 4, is applied to a wound and the physiological fluids present in the wound area immediately contact the silver and other metal particles, 20 and 30, and/or begin to erode the polyalkylene coating on the particles in the carrier layer 10. This erosion begins a controlled release of the silver and other metal particles, 20 and 30, from the carrier layer 10. The silver and other metal particles, 20 and 30, are not absorbed systemically by the body. A galvanic current of approximately 0.2 millivolts will form in the physiological fluids at the wound site. The galvanic current may range from 0.1 to 1.0 millivolts. The galvanic current performs as an antimicrobial against bacteria, viruses, fungi. Without intending to be bound by theory, the antimicrobial action occurs as follows: all bacteria, viruses, and fungi are negatively charged, so when the microbes are in the vicinity of an anode and a cathode (the silver and other metal particles, 20 and 30) and the resulting galvanic current, the negatively charged microbes migrate to and adhere to the silver particles 20. The action of the silver particles 20 on the microbes is to interfere with the function of the Sulfhydryl (SH) groups of the microbes, and thus to interfere with the respiratory pathway of the organisms to kill the organisms. Along with their microcidal properties, the silver particles 20 draw edema fluid from the wound area to decrease swelling which increases the capillary blood flow which promotes healing. Furthermore, ions from the other metal particles 30, provide, in the case of zinc, therapeutic benefits including but not limited to, control of viruses and autolytic debridement of wounds and scar tissue. In the preferred embodiment, zinc is used because zinc is necessary for a wide variety of metabolic processes, including the synthesis as well as the degradation of nucleic acids, proteins, carbohydrates, and lipids. Zinc is also necessary for the synthesis of MMPs (metaloproteinase) which remodels the wound by degradation of nucleic acids, proteins, lipids, carbohydrates, and other breakdown products secondary to the cell destruction associated with wound healing. Zinc also adds a further bacteriocidal effect to the wound area. The high prevalence of zinc in mammal tissue speaks to its importance and role as a nutrient. Likewise, trace minerals from metals such as copper also affect tissue function. The direct application of the bimetallic bandage or gauze, 2 or 4, along with the hydrophilic polymer of the carrier layer 10 keeps the wound moist which aids healing. The galvanic current that results also decreases local pain much like a tens unit, which in turn decreases any limitation of movement, which also assists wound healing.

The wound bandage or gauze, 2 or 4, of the present invention potentially obviates the need for conventional antimicrobial agents to be administered, either systemically or topically. However, the combination of antimicrobial agents, such as antibiotics, with the present invention may be desired in some cases.

The production of a galvanic current by the present invention should be readily appreciated by one skilled in the art of electrochemistry. However, a brief overview is provided as follows: once the silver metal particles 20 and the other metal particles 30 are uncovered and activated by an electrolyte-containing fluid, such as edema fluid, plasma, or blood which contains approximately 0.9% NaCl, ions are released. An electrical connection is formed between the particles and an electric current flows. Ions of the more active metal, the silver metal particles 20, which forms the anode, are transferred to the electrolyte to the less active metal, the other metal particles 30 as the cathode. The movement of the ions creates an electrical galvanic current that produces a wound healing effect as discussed herein.

The presence of the silver anode, via the silver metal particles 20, and the zinc cathode, via the other metal particles 30, creates a wet battery when moistened by wound exudate, thereby augmenting the current of injury by approximately one and a half microvolts which increases the deposition of the metal ions into the wound bed by iontophoresis. This deposition is in addition to the normal diffusion of the metal ions.

Although some of the silver and other metal particles, 20 and 30, may not be completely coated in the pre-cured polyalkylene of the carrier layer 10, enough of the particles, 20 and 30, are coated so that the uncovering of the particles via erosion occurs as a sustained or controlled release process while the wound dressing bandage 2 or gauze 4 is in place over the affected area. In other words, when the silver and other metal particles, 20 and 30, are brought adjacent to one another through sustained erosion of the polyalkylene of the carrier layer 10, a sustained and extended release of galvanic current is produced. Therefore, the controlled release of the silver and other metal particles, 20 and 30, is essential to the present invention. The eroding action of physiological fluids in or at the wound site, as well as simple agitation or abrasion, will release the silver and other metal particles, 20 and 30, from the polyalkylene of the carrier layer 10. As previously discussed herein, other polyalkylene materials besides polypropylene, such as polyethylene, may be used for the carrier layer 10, but polypropylene is preferred. The polypropylene of the carrier layer 10 may be cured in situ, after the metals are deposited as desired, by air drying, heat curing, or other polyalkylene polymer curing methods now known or heretofore developed in the art.

The controlled, sustained galvanic current created by the bandage or gauze, 2 or 4, of the present invention also enhances wound healing as follows: when the plasma or other physiological fluids in the wound come into contact with current produced by the present invention, the fluids become hypertonic. The hypertonicity draws inflammation-related edema out of the wound area. The drawing of edema from the wound area not only moistens the wound edges of the tissues, but also decreases the pressure on the capillaries thereby allowing increased blood flow within the affected tissue, both of which enhance the healing process.

While generally the bandage or gauze, 2 or 4, and outer layer 6 will be made of the same polyalkylene polymer as is used in the carrier layer 10 for the silver and other metal particles, 20 and 30, a different polymer may be used for the outer layer 10. Further, the outer layer 10 need not be made of a polyalkylene at all, but may be composed of any bioabsorbable or biocompatible material, such as collagen, intended either to erode during healing or to remain in situ after healing has been realized. For example, coated biocompatible materials such as those which bear lactoferrin or transfer factor to create a matrix for blood coagulation may be used with the present, or subsequently developed improvements to, two-metal polyalkylene-borne arrays. Other matrix or derivatization materials may be incorporated in such bioabsorbable or biocompatible materials. The gauze 4 embodiment may be used to fill deep wounds such as bullet holes or other blunt trauma wounds that create large cavities, and can either absorb over time or can remain in place as the tissue regrows. The gauze 4 embodiment can be applied to abrasions and burns and left in place for several days, thereby facilitating healing by not disturbing the wound bed with daily changes. The gauze 4 embodiment can also be used (rolled, unrolled, folded together, etc.) for puncture wounds, deep wounds, and tunnel wounds that are ordinarily difficult to adequately dress. The polyalkylene material of the carrier layer 10 remains the same, however, to ensure a controlled exposure of the metals over time and concomitant sustained creations of the galvanic current.

For the wound bandage or gauze, 2 or 4, of the present invention intended for eventual removal, the antimicrobial action will persist and makes it suitable to leave in place for up to ten days. If necessary, the wound bandage or gauze, 2 or 4, may even be rinsed with water and reapplied in settings in which a substitute wound bandage or gauze, 2 or 4, is not available, such as in combat. Additionally, because of the inherent antimicrobial character of the present invention, it can even be used in emergencies and dire circumstances as an emergency water purification filter. When water that is potentially contaminated with microbes is to be rendered potable, the water may be poured through the carrier layer 10 of the present invention and collected in a clean container for safe use. It is believed that the exposure of the microbes to the electrical current formed by the silver and other metal particles, 20 and 30, kills and/or removes enough microbial contamination from the water to make nonpotable water generally potable. While there may be limitations on the ability of the present invention to purify water under some conditions, this disclosure of gross decontamination action should be understood as an emergency field measure when no other water purification equipment or chemicals are available. Such conditions would foreseeably arise under the same circumstances as would the need for wound dressing materials, namely, armed services deployment conditions of all kinds.

The presently preferred embodiment of the present invention is illustrated in FIGS. 1-2, wherein the wound dressing bandage 2 has an outer layer 6 composed of a hydrophillic, vapor-permeable polymer of polyethylene or polypropylene. The outer layer 6 allows vapor to escape the bandage 2 and also provides for absorption of excess fluid. The carrier layer 10 of the presently preferred embodiment of the present invention is composed of fluid-soluble pre-cured polypropylene or pre-cured polyethylene. The carrier layer is of a sufficient thickness 12 to allow the suspended silver particles 20 and other metal particles 30 to be suspended in multiple horizontal zones throughout the carrier layer 10. Individual spots or aliquots of the silver particles 20 and other metal particles 30 should be spaced in portions by which the metal types alternate and the spots or aliquots range in spacing less than 2.0 mm apart without touching. The silver particles 20 of the presently preferred embodiment are silver that is at least 99.99% to 99.9999% pure. The other metal particles 30 of the presently preferred embodiment are zinc that is at least 99.99% to 99.9999% pure. In the presently preferred embodiment, the diameter of the silver particles and the zinc particles is between 0.1 to 1.0 microns. The adhesive portion 50 of the presently preferred embodiment is present along the skin surface side of the bandage 2. The electrolyte of the presently preferred embodiment is edema fluid, plasma, or blood present at the wound site having a NaCl content of approximately 0.9%.

In another non-limiting embodiment of a wound dressing bandage or gauze, 2 or 4, of the present invention, the silver particles 20 and the other metal particles 30 are held separately in a carrier layer 10 of a porous bioresorbable mixture of copolymers, polylactic acid (PLA) and polyglycolic acid (PGA). The building agent solvent is ethyl acetate. The copolymers in a specific ratio form a hydrolytically biodegradable porous sponge-like material that degrades the lactic acid present in the wound fluid. The copolymer mixture containing the metals is ejected from an ink-jet print head. Each metal is deposited separately in a specific pattern by a modified silk screening process. The binding solvent ethyl acetate evaporates during the printing process. The silver particles 20 and the other metal particles 30 which are held separately in the copolymer deposits are uniformly released as the copolymer mixture is degraded by the wound fluid. The silver particles 20 and the other metal particles 30 are uniformly released separately into the electrolyte containing wound fluid creating a sustained galvanic current. The wound dressing bandage or gauze, 2 or 4, remains electrically active for 10 to 14 days, thus the dressing only has to be changed weekly. If the dressing becomes obstructed with blood products it can be rinsed with water and reapplied and will continue to function. The lactic acid produced from the breakdown of the copolymer reservoirs is anti-microbial as well as a stimulant to cell growth. The persistent moist surface created on the wound also supports cell growth and prevents any adherence of the new cells to the wound dressing bandage or gauze, 2 or 4, when it is removed. The active bimetallic surface is placed directly on the wound surface. The outer layer 6 of the present embodiment is a thin hydrophilic layer of sodium polyacrylate that absorbs the excess wound fluid. The wound dressing bandage or gauze, 2 or 4, is held in place by an elastic adhesive portion 50 that moves with the patient.

The following Examples further illustrate studies of the present invention:

EXAMPLE 1

Figure 6:
FIG. 6 is a photographic illustration of a necrotic area after toe amputation.
Figure 7:
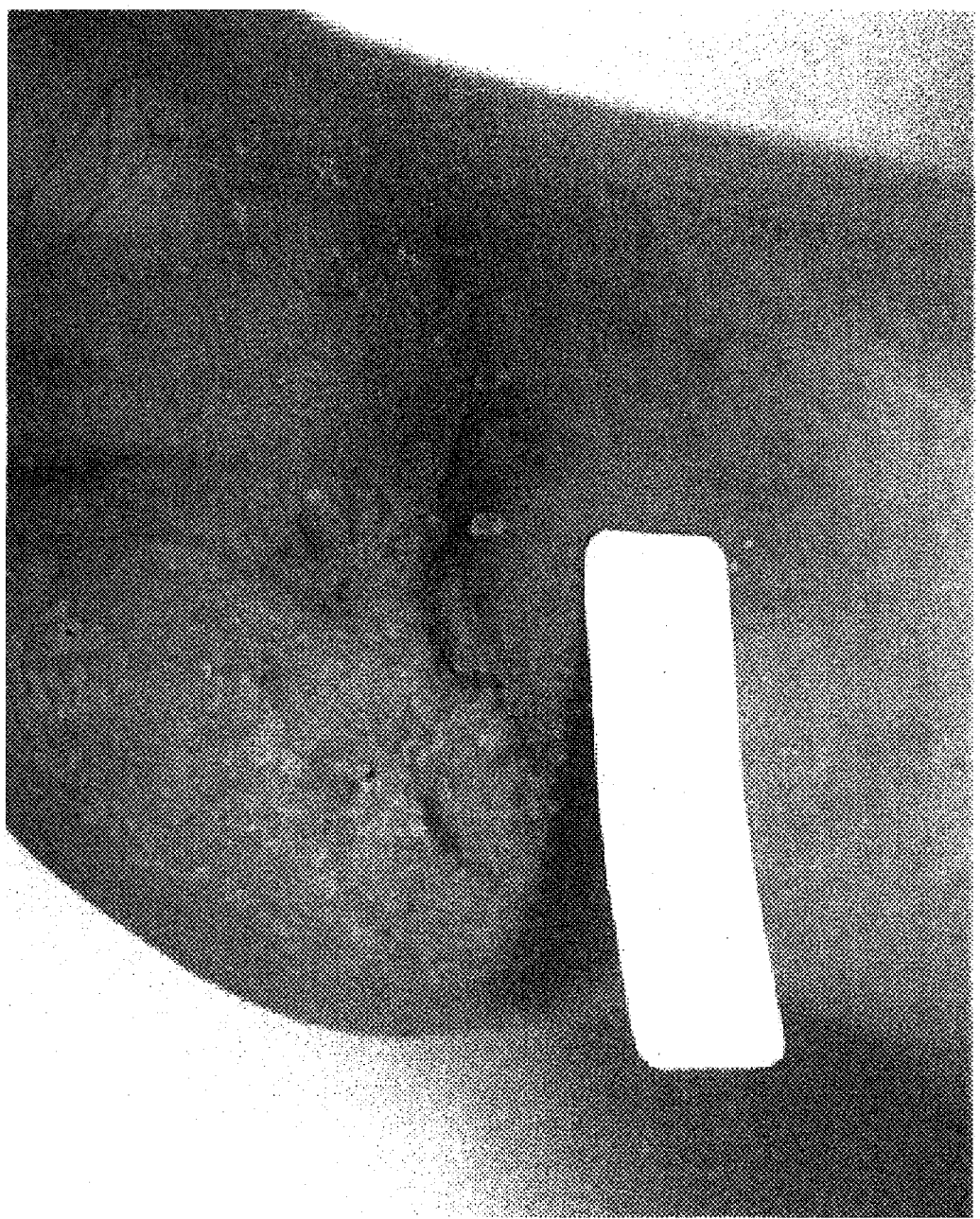
FIG. 7 is a photographic illustration of the toe area of FIG. 6.

As shown in FIG. 6, a 64 year old male with Type II diabetes had a necrotic toe amputated. The wound did not heal for over eight months. The patient was scheduled for a below the knee amputation. The patient sought out the medical services of the inventor, had the wound debrided and the osteomyelitis associated with necrotic tissue removed. The inventor packed the wound with the gauze of the present invention as experimental treatment. As shown in FIG. 7, after five months of gauze treatment, the wound was healed.

EXAMPLE 2

Figure 8:
FIG. 8 is a photographic illustration of a burnt calf area.
Figure 9:
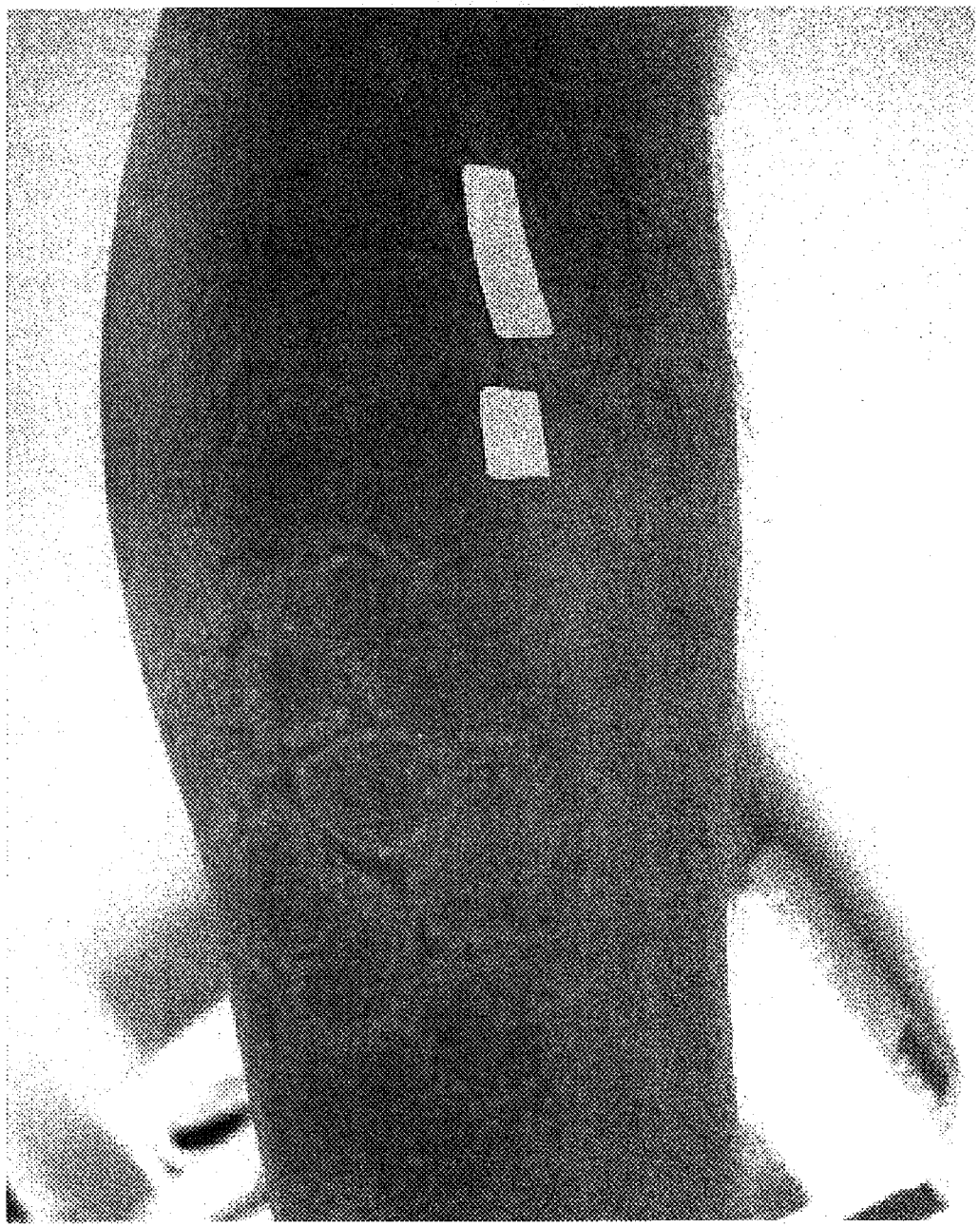
FIG. 9 is a photographic illustration of the burnt calf area of FIG. 8.

As shown in FIG. 8, a 25 year old male in good health crashed his motorcycle and sustained a $3^{rd}$ degree burn of his lower calf. He was told he needed a skin graft and would be off of his feet for seven weeks, which the patient could not afford. The patient sought out the medical services of the inventor who cleaned the wound and applied the gauze of the present invention. Within two days the patient was able to walk. FIG. 9 was taken roughly two weeks into the experimental treatment. With continued treatment, the skin became healthy with no pigment change, no pain, and no limitation of motion.

EXAMPLE 3

Figure 10:
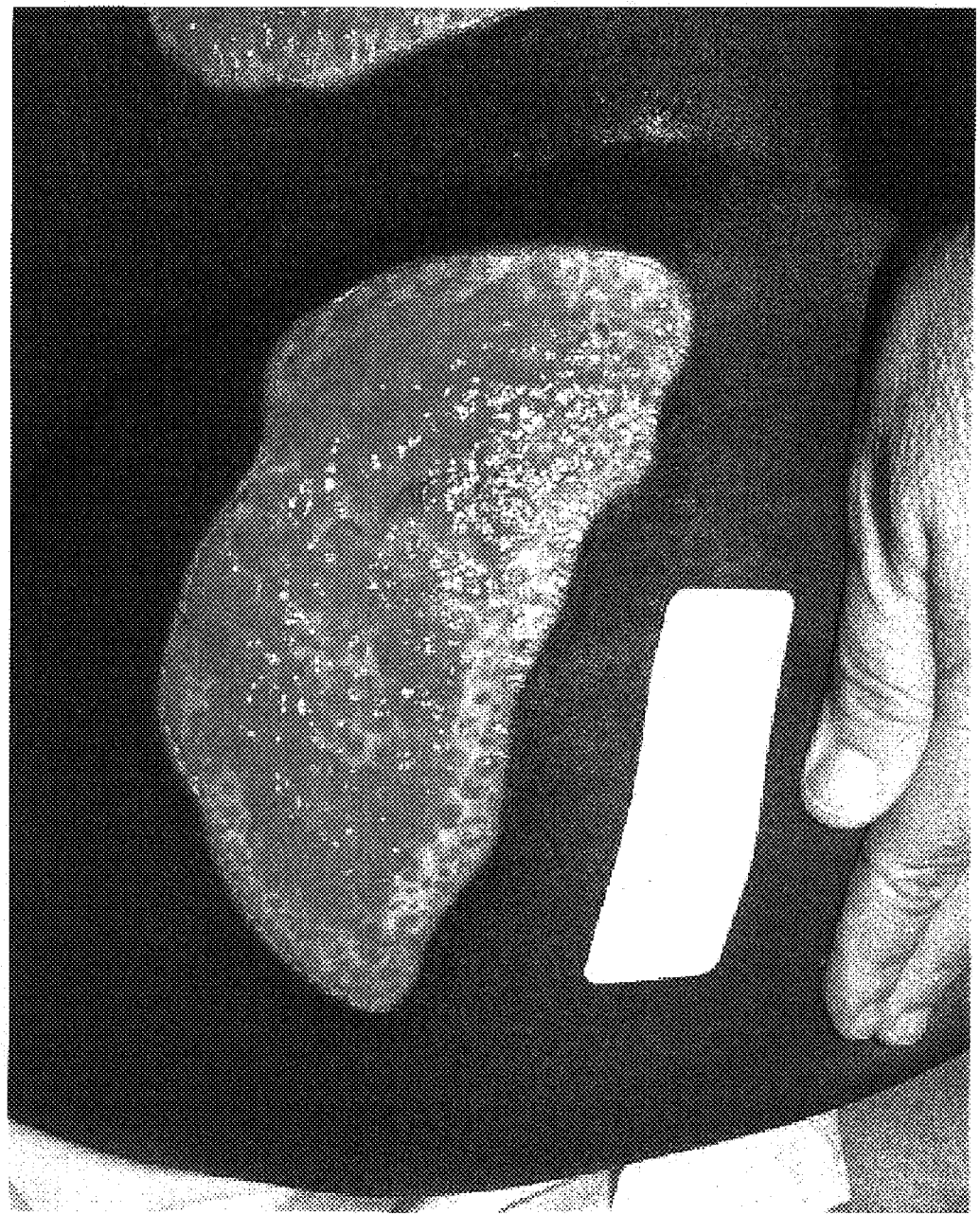
FIG. 10 is a photographic illustration of a burnt buttock area.
Figure 11:
FIG. 11 is a photographic illustration of the burnt buttock area of FIG. 10.
Figure 12:
FIG. 12 is another photographic illustration of the burnt buttock area of FIG. 10.

As shown in FIG. 10, a female patient presented with a third degree and fourth degree burn to the buttock area that would not respond to conventional treatment. As shown in FIGS. 11 and 12, within weeks of experimental treatment with the present invention, the treated area had healed significantly with minimal scarring and without loss of pigmentation.

EXAMPLE 4

The kinetics of the release of silver ions from the nylon fiber material of the present invention was examined by atomic absorption spectrometry over a time interval of 24 hours. It was calculated that approximately 0.5% of the total silver present was released in the first hour of extraction. The silver extract gave a shorter delay in the onset of killing all bacteria and greater rate of killing than the control, which was silver nitrate. After 24 hours approximately 1.0% of the total silver-zinc content was released. Release was inhibited by the accumulation of ions in solution (0.9% Normal Saline) and only slightly limited by the amount of silver available for extraction. Because the killing properties of the silver-zinc combination are so potent in dilute solution, it is not the amount of silver ions released, but the time duration of release that is important. The silver-zinc bandage does not have to be changed for seven to ten days, thereby minimizing disturbance of the wound bed, decreasing nursing care, and eliminating the use of antibiotics. The silver anode binds to the wound bed serum proteins or it is precipitated by reaction with chloride anions, so that silver is not absorbed in the body. Slow and consistent delivery of silver and zinc ions to the wound surface over time is most beneficial to wound healing.

Prior to use of the wound bandage or gauze, 2 or 4, of the present invention, it may be desirable to activate the wound bandage or gauze, 2 or 4, of the present invention by delivering a suitable liquid such as water, saline solution and solution or lactated saline solution (Ringer's Solution) to the carrier layer 10. In some cases, it may be desirable to provide other metals via the liquid. The activating liquid can also comprise drugs or agents for therapeutic effects or to retain moisture such as sugar, or to provide nutrition directly to tissue, such as fetal calf serum. When the wound bandage or gauze, 2 or 4, of the present invention is used in a moist environment, i.e., where substantial blood, saliva, sweat or other liquid is present, application of liquid prior to use may not be necessary.

An important advantage of all embodiments of the present invention is that they provide sustained release therapeutic and/or antibacterial, antifungal and antiviral properties without the need for an external power source. This reduces the cost of devices, simplifies uses and enhances reliability. It is understood that the specification and drawings are illustrative of, but do not limit, the present invention, and other embodiments and variations are within the spirit and scope of the present invention.

The present invention has been described with reference to the preferred embodiments. Obvious modifications, combinations or alterations will occur to others upon reading the preceding detailed description. It is intended that the invention be construed as including all such modifications, combinations and alterations insofar as they come within the scope of the appended claims or the equivalents thereof.

The invention claimed is:

1. A wound dressing, comprising:
a carrier layer, said carrier layer including a plurality of first metal particles having an electrochemical potential, a fluid soluble material, and a plurality of second metal particles having a different electrochemical potential from said plurality of first metal particles,
wherein said first metal particles and said second metal particles are suspended alternatively within said fluid soluble material, wherein said fluid soluble material is comprised of a bioresorbable mixture of polylactic and polyglycolic acid and further wherein said first metal particles and said second metal particles are spaced from between 0.1 mm to 7.0 mm apart and due to their spacing generate a sustained galvanic current of between 0.1 to 1.0 millivolts when subjected to an electrolyte-containing fluid causing erosion of said carrier layer.

2. The wound dressing of claim 1, wherein an outer layer is present adjacent said carrier layer and said outer layer material is selected from the group consisting of polypropylene, polyethylene, polyethylene terephthalate, rubbers, copolymers and silicones.

3. The wound dressing of claim 1, wherein said first metal particles are selected from the group consisting of silver, and salts and oxides thereof.

4. The wound dressing of claim 1, wherein said second metal particles are selected from the group consisting of aluminum, cobalt, copper, gold, iron, magnesium, platinum, titanium and zinc, and salts and oxides thereof.

5. The wound dressing of claim 4, wherein said zinc salts and oxides thereof enable the remodeling of a wound surface via synthesis of one or more metalloproteinases.

6. The wound dressing of claim 1, wherein said wound dressing is a bandage having an adhesive portion.

7. The wound dressing of claim 1, wherein said outer layer material is a polyacrylate salt.

8. The wound dressing of claim 1, wherein said galvanic current causes pathogens to migrate to an anode to be destroyed.

9. A method of treating a patient with a wound dressing, comprising the steps of:
(i) providing to a patient a wound dressing comprising,
a carrier layer, said carrier layer including a plurality of first metal particles having an electrochemical potential, a fluid soluble material, and a plurality of second metal particles having a different electrochemical potential from said plurality of first metal particles, further wherein said first metal particles and said second metal particles are spaced from between 0.1 mm to 7.0 mm apart,
wherein said first metal particles and said second metal particles are suspended alternatively within said fluid soluble material, whereby a sustained-release galvanic current of between 0.1 to 1.0 millivolts is produced between said first metal particles and said second metal particles when said carrier layer is subjected to electrolyte-containing fluids causing erosion of said carrier layer, wherein said carrier layer fluid soluble material is comprised of a bioresorbable mixture of polylactic acid and polyglycolic acid;
(ii) applying to said patient said wound dressing; and
(iii) removing said wound dressing from said patient at seven to ten days after step (ii).

10. The method of treating a patient with a wound dressing of claim 9, wherein an outer layer material adjacent said carrier layer is selected from the group consisting of polypropylene, polyethylene, polyethylene terephthalate, rubbers, copolymers and silicones.

11. The method of treating a patient with a wound dressing of claim 9, wherein said first metal particles are selected from the group consisting of silver, and salts and oxides thereof.

12. The method of treating a patient with a wound dressing of claim 9, wherein said second metal particles are selected from the group consisting of aluminum, cobalt, copper, gold, iron, magnesium, platinum, titanium and zinc, and salts and oxides thereof.

13. The method of treating a patient with a wound dressing of claim 9, whereby upon performing step (ii), said galvanic current augments a naturally produced current of injury and applies said galvanic current to a wound surface to stimulate the liberation of substance P thereby enhancing wound healing by stimulating cell growth and keeping said wound surface sterile.

* * * * *